United States Patent [19]

Luss

[11] Patent Number: 4,500,517

[45] Date of Patent: Feb. 19, 1985

[54] ANTIMICROBIAL COMPOSITION FOR A SEMIPERMEABLE MEMBRANE

[75] Inventor: V. Gerold Luss, Minneapolis, Minn.

[73] Assignee: H. B. Fuller Co., St. Paul, Minn.

[21] Appl. No.: 327,796

[22] Filed: Dec. 7, 1981

[51] Int. Cl.³ ............................................. A01N 59/02
[52] U.S. Cl. .................................................... 424/162
[58] Field of Search ........................................ 424/162

[56] References Cited

U.S. PATENT DOCUMENTS 2,139,102 12/1938 Reynolds et al. ................... 424/162
3,105,790 10/1963 Bartholomew ..................... 424/162
3,928,577 12/1975 Kochurova et al. ................ 424/162
4,128,397 12/1978 Lynch ................................. 424/162
4,304,673 12/1981 Reynolds et al. ................... 424/162

Primary Examiner—Elbert L. Roberts
Attorney, Agent, or Firm—Merchant, Gould, Smith, Edell, Welter & Schmidt

[57] ABSTRACT

An antimicrobial composition useful to prevent microorganism growth on semipermeable membranes comprises an aqueous medium having a pH of less than 4.5 and sulfurous acid or a source of sulfurous acid.

19 Claims, No Drawings

ANTIMICROBIAL COMPOSITION FOR A SEMIPERMEABLE MEMBRANE

FIELD OF THE INVENTION

This invention relates to semipermeable membranes used in membrane separation processes including ultrafiltration and reverse osmosis.

BACKGROUND OF THE INVENTION

Semipermeable membranes, in ultrafiltration and reverse osmosis processes, have been used in the past for the separation or concentration of a variety of substances including those which can support the growth of microorganisms.

Osmosis is a process which can operate by confining or restraining a fluid with a semipermeable membrane designed to permit the passage through the membrane of certain fluid constituents while preventing the passage of other constituents. A semipermeable membrane separating two solutions of differing concentrations or solvent activities permits the solvent to flow from the more dilute solution through the membrane into the more concentrated solution allowing the concentration on either side of the membrane to equilibrate.

In reverse osmosis, pressure is deliberately applied to the more concentrated solution causing the flow of solvent in the opposite direction through the membrane, i.e. into the more dilute solution. In this way the diluent liquid can be separated from dissolved species, increasing the concentration of the species in solution. Reverse osmosis is ideal for sensitive biochemical and organic compositions since it relies on pressure rather than heat or other energetic processes. Reverse osmosis also has the substantial benefit, in comparison to other water separation processes such as distillation and freeze drying, of being a process having low energy consumption.

Ultrafiltration is a filtration process for the removal of particles that are unfilterably small for conventional filtration processes.

Semipermeable membranes provide an ideal environment for the growth of a variety of microorganisms in and on the surfaces of the membrane when contacted with a solution containing nutrient components. The membranes are flawed by small microscopic pores which can cause some minor leaks and some small amount of mixing between the solutions on either side of the membrane. Accordingly, while one side of the membrane is exposed to the high concentrations of the dissolved, commonly nutrient species, a small concentration of the dissolved nutrient species can appear on the reverse of the membrane.

A colony of microorganisms can begin to grow around a small particle of a nutrient substance from the solution, on either side of the membrane. As the microorganisms grow and divide, supported by nutrients in the fluid, the colony can spread across the surface. The rate of flow of fluid through the membrane can be reduced in direct relationship to the surface area covered by or lost to the microorganism colonies. Since the efficiency of the reverse osmosis or ultrafiltration process is directly related to the flow rate of liquid through the membrane any reduction in fluid flow rate is highly undesirable. Further microorganism growth can spoil the fluid and constituent being separated or concentrated using the membrane.

Microorganism colonies can be removed from semipermeable membranes by mechanically or abrasively removing the microorganisms or by back flushing the reverse osmosis systems. However, these methods are inappropriate since semipermeable membranes are delicate, can be damaged by reverse flushing and can be destroyed by mechanical abrasion.

Chemical means for preventing or destroying microorganism growth have been used by contacting chlorine, formaldehyde hydrogen peroxide, etc. with the membranes. These chemicals can be harmful to operating personnel and can damage both the semipermeable membrane and substances and diluents in contact with the membrane.

Since the microbial growth can occur on either side or within the membrane, in order to be effective in killing microbs in the units when only one side of the membrane is available to treatment the antimicrobial composition must be able to pass through the membrane. Most common antimicrobial compounds comprising organic molecules having molecular weight greater than about 150 cannot successfully prevent or destroy microbial growth within membranes and on both surfaces since they cannot pass through the membrane.

A need exists for an effective, safe membrane-compatible composition which can be used to prevent or destroy microorganism growth in and on semipermeable membrane surfaces.

SUMMARY OF THE INVENTION

I have now found that a composition comprising an aqueous solution having a pH of less than about 4.5 of an effective antimicrobial amount of sulfurous acid or a sulfurous-acid yielding compound, when contacted with a membrane substantially prevents the growth of or destroys colonies of microorganisms which can reduce the rate of flow of liquid through the membrane. We have found that the sulfurous acid molecules in solution have a molecular size which permits the sulfurous acid molecules to penetrate the membrane, and to come into intimate contact with the microbial growth.

A first aspect of the invention is an antimicrobial membrane preservative composition which comprises an aqueous solution having a pH less than about 4.5 of sulfurous acid or a source of sulfurous acid. A second aspect of the invention comprises a process for preventing or killing the growth of microorganisms on and in a semipermeable membrane by contacting the membrane, in the unit in which it is used or separate from the unit, with a composition comprising an aqueous solution, having a pH less than 4.5, of sulfurous acid or a source of sulfurous acid. A third aspect of the invention is a solid or liquid concentrate comprising sulfurous acid or source of sulfurous acid which when dissolved, diluted or suspended in liquid provides an effective antimicrobial amount of sulfurous acid at a pH less than about 4.5 solution. The concentrate can also comprise a suitable buffer.

By aqueous solution, I mean that the antimicrobial compositions of this invention comprise a major portion of water. The compositions can also contain a compatible cosolvent such as an alcohol, a ketone, etc.

DETAILED DESCRIPTION

Sulfurous Acid Compounds

Sources of sulfurous acid useful in the invention provide sulfurous acid at a pH less than about 4.5 at a temperature, and other conditions, common in units having semipermeable membranes. Examples of sulfurous acid-yielding compounds include sulfur dioxide ($SO_2$), sulfurous acid ($H_2SO_3$), sodium sulfite ($Na_2SO_3$), sodium sulfite hydrate ($Na_2SO_3 \cdot XH_2O$ wherein X commonly is 7 or less), sodium bisulfite ($NaHSO_3$) and sodium bisulfite hydrate ($NaHSO_3 \cdot XH_2O$, wherein X is 7 or less), sodium metabisulfite, also known as sodium pyrosulfite ($Na_2S_2O_5$) and its hydrates, etc. Sulfurous acid and sources of sulfurous acid can be encapsulated in particles comprising a coating which surrounds the sulfurous acid or sulfurous acid-yielding compound, and dissolves or disrupts in water to release sulfurous acid into solution. See Kirk-Othmer *Encyclopedia of Chemical Technology*, 2nd Edition, Volume 19, pp. 407-421 for a discussion of sulfur oxides and sulfur acids.

Buffer Systems

It is well known that in aqueous systems the concentration of sulfurous acid decreases as pH increases. Accordingly the antimicrobial membrane preservatives of this invention can beneficially be maintained at a pH less than about 4.5, preferably at a pH less than about 3.5 and most preferably at a pH between about 2.0-3.5. Well known, commonly available buffer systems can be used to maintain the pH of these systems, however I have discovered preferred buffer systems which provides pH control, the ability to sequester alkaline earth metal ions which can precipitate in the presence of sulfite ($SO_3=$) ions and additional antimicrobial activity. The preferred pH control buffer systems of this invention comprises a water-soluble polycarboxylic acid, an ammonium or alkali metal salt of a carboxylic acid and optionally a anionic, nonionic, cationic, or amphoteric surfactant or surface active agent.

Polycarboxylic Acids

Polycarboxylic acids that are useful in forming the buffer systems in the antimicrobial compositions of this invention include water soluble compounds represented by the formula:

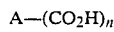

$$A-(CO_2H)_n$$

wherein A comprises a polyvalent substantially hydrocarbon radical and n comprises an integer of 2 to 6. By water soluble, I mean that the polycarboxylic acid compounds useful in the membrane preservatives of this invention are present in solution to the extent that the solution has a pH less than about 4.5. The substantially hydrocarbon radical can contain a variety of substituents which do not prevent the water solubility or membrane permeability of the polycarboxylic acid, such as hydroxy (—OH), alkoxy (—O—R), acyl(—CO—R), nitro (—$NO_2$), carbonyl (—C=O), etc.

A preferred property of the polycarboxylic acid is its ability to complex or sequester alkaline earth metal or other ions which will precipitate, in the presence of sulfite ($SO_3=$) ions, as an alkaline earth metal sulfite. By-products such as whey and industrial waste water can commonly contain substantial quantities of calcium or magnesium or other multivalent metal ions. Sulfurous acid reacts with such ions to form an insoluble sulfite precipitate which can plug semipermeable membranes. Sequestering or complexing amounts of a polycarboxylic acid can maintain alkaline earth metal compounds soluble in the presence of sulfites ($SO_3=$) ions.

Suitable water soluble, alkaline earth metal sequestering, polycarboxylic acids include dicarboxylic, tricarboxylic tetracarboxylic acids etc.. Useful dicarboxylic acids include oxalic acid, succinic acid, tartaric acid, glutaric acid, adipic acid, malonic acid, maleic acid, water soluble phthalic acid derivatives including bromophthalic acid, benzoylphthalic acid, chlorophthalic acid, 4-nitrophthalic acid, etc. Useful tricarboxylic acids include water soluble sources of 1,2,3-propane tricarboxylic acid and derivatives thereof including citric acid (2-hydroxy-1,2,3-propane tricarboxylic acid), water soluble derivatives of trimellitic acid (1,2,4 benzene tricarboxylic acid), and nitrilotriacetic acid (NTA). Useful tetracarboxylic acids include ethylene diamine tetracarboxylic acid and related compounds.

Carboxylic Acid Salts

Carboxylic acid salts useful in this invention include ammonium and alkali metal carboxylates formed from water soluble carboxylic acids having 1 to 8 carbon atoms. Examples of suitable carboxylic acids include formic acid, acetic acid, propionic acid, butyric acid, isobutyric acid, trichloroacetic acid, trifluoroacetic acid, ethoxyacetic acid, gluconic acid, cyanobenzoic acid, cyanoacetic acid, vinylacetic acid, phenoxyacetic acid, hydroxyacetic acid, dehydroacetic acid, etc. An important characteristic of the carboxylic acid salts of this invention is that at the pH of the antimicrobial composition, less than 4.5, a sufficient antimicrobial amount of the carboxylic acid is present in equilibrium with the salt of the carboxylic acid in the aqueous system.

Surfactants

The surface active agents that are useful in this invention to increase the wetting characteristics of the antimicrobial composition comprise common anionic, cationic, amphoteric, and nonionic surface active compositions compatible with the membrane. An excellent discussion of surfactants or surface active agents is disclosed in Kirk-Othmer, *Encyclopedia of Chemical Technology*, Second Edition, Volume 19, pp. 507-593.

Briefly, examples of anionic surfactants include carboxylic acids and salts, sulfonic acids and salts, sulfuric acid esters and salts, and phosphate esters and salts. For example, amino carboxylate surfactants N-acylsarcosinate surfactants, acylated protein hydrosylates, linear alkyl sulfonates, alkyl benzene sulfonates, etc.

Nonionic surfactants have essentially no charge when dissolved or dispersed in aqueous media. The hydrophilic tendency of nonionic surfactants is due to primarily oxygen atoms in the molecule which hydrate by hydrogen bonding to water molecules. Examples of hydrophilic moieties in nonionic surfactants are ether groups, hydroxyl groups, ester linkages, amide linkages, etc. Specific examples of nonionic surfactants are polyoxyethylene surfactants prepared from ethylene oxide, ethoxylated alkyl phenols, for example nonylphenoxy-polyethyleneoxy ethanols, ethoxylated aliphatic alcohols, carboxylic acid esters, carboxylic acid amides, polyoxyalkyleneoxide block-copolymers, etc.

Amphoteric surfactants contain at least one acidic and at least one basic hydrophilic moiety in their structure. These ionic functions may be any of the anionic or cationic groups common in surfactants and the molecules can contain one or more of either a cationic or anionic function. Examples of suitable amphoteric surfactants include N-coco-3-aminopropionic acid and salts thereof and N-tallow-3-iminodipropionate, propoxylated and sulfated oleic acid-ethylene diamine condensate, amino acid based surfactants such as the betaines or Tegos based on glycerines, etc.

Cationic surface active agents can be used, however, many cationic surface active agents suffer from film-forming characteristics which reduces their applicability in the antimicrobial compounds of this invention.

Membranes

The antimicrobial compositions of this invention can be used to prevent or destroy microbial growth in and on all common semipermeable membranes including reverse osmosis and ultrafiltration membranes prepared from polysulfone polymers, poly(ether/amide) polymers, poly(ether/urea) polymers, polyamide polymers and membranes prepared from cellulose and cellulose derivatives such as cellulose acetate, carboxymethylcellulose, etc.

Compositions

The antimicrobial compositions for semipermeable membranes of this invention comprise an aqueous solution having about 0.01 to 10.0 wt-% of sulfurous acid or the source of sulfurous acid ($H_2SO_3$) and the pH controlling buffer system which can comprise 0.01 to 5.0 wt-% of a polycarboxylic acid and 0.01 to 5.0 wt-% of a water soluble ammonium or alkali metal salt of carboxylic acid. Preferably, the antimicrobial composition comprises a major portion of water, about 0.1 to 1.0 wt-% of sulfurous acid or a sulfurous acid-yielding compound, about 0.1 to 1.0 wt-% of a polycarboxylic acid, and 0.1 to 1.0 wt-% of ammonium or alkali metal carboxylate. Most preferably the antimicrobial composition comprises a major portion of water, 0.25 to 0.75 wt-% sulfuric acid or sulfurous acid-yielding compound, 0.25–0.35 wt-% polycarboxylic acid, 0.10 to 0.20 wt-% ammonium or alkali metal carboxylic acid salt. Optionally the agent of this invention can also contain an effective wetting amount, comprising about 0.001 to 1.0 wt-%, preferably 0.01 to 1 wt-%, of surfactant.

The membrane preservatives of this invention can be formulated in a dry blend or concentrate in an aqueous concentrate. Dry blend forms of the membrane preservative can comprise 45 to 95 weight-% of a source of sulfurous acid, 5 to 50 weight-% of a polycarboxylic acid, 1 to 50 weight-% of a water soluble ammonium or alkali metal carboxylate and optionally 0.01 to 10 weight-% of a surfactant. Concentrates of the composition in a suitable solvent such as water can contain a major portion of a suitable solvent such as water and about 20-80 weight-% of the solid dry blend concentrate. Both the dry blend concentrate, and the aqueous concentrate in solvent can be dissolved or diluted in additional quantities of solvent to prepare a solution, containing 0.01 to 50 wt-% of sulfurous acid or a sulfurous acid-yielding compound, which can be directly contacted with semipermeable membranes to preserve the membrane and prevent or destroy the growth of microorganisms.

The reduction in efficiency of semipermeable membrane processes caused by microorganism colonies can be observed in a variety of ways. The fluids are contacted within the membrane, at a pressure of 10-1000 lbs. per square inch, within the reverse osmosis unit in order to provide the reverse osmosis effect or within the ultrafiltration unit. It is important to maintain the flow of fluid through the membrane at a high rate (indicate common rates per square inch of membrane) in order to derive maximum benefits from the processes. The growth of microorganisms on the membranes can often be detected when the flow of fluid through the membrane decreases about 10–20%, often the flow can be reduced by as much as 50%. Fluids contacted with reverse osmosis units are split into at least two streams, one having substantial increase in solute concentration and another having very low concentration of solute. In the instance that a valuable solute is being concentrated by reverse osmosis, it is important to separate the maximum amount of water resulting in high solute concentration. Accordingly, as the membrane is covered by the growth of microorganisms the concentration of the valuable compounds will decrease since solvent is removed more slowly. Crude production biological compositions such as whey or antibiotics commonly are produced at a concentration of about 0.1 to 7 wt-%. Using reverse osmosis the concentration of the valuable compound can easily be increased to about 12 to 36 wt-%. However, as the membrane becomes covered by the growth of microorganisms the efficiency of the unit and the associated concentration of valuable compound in the aqueous stream can often be reduced to about 4 to 10 wt%.

Similarly in ultrafiltration processes, the flow of solvent through the membrane can be prevented or substantially reduced in the presence of microbial colonies covering the membrane.

Upon the observation of the reduction in efficiency, caused by the microorganism growth in either the water flow rate or the solute concentration, the semipermeable membranes can be removed from the unit and can be contacted with the antimicrobial composition of the invention. The membranes having microbial colonies can preferably be flushed with water or suitable detergents in order to remove the process fluids. The membrane can then be contacted with the antimicrobial composition of the invention.

Alternatively, the membrane with the harmful colonies of microorganisns can be contacted with the composition of this invention at ambient or elevated temperatures and pressures in situ. The antimicrobial compositions of this invention can be applied to the membrane as a soak solution during a time when the unit is not in operation.

After soaking the composition can be removed and the unit can be returned to service without bacterial contamination. In another mode, the microorganism covered membrane, in its reverse osmosis or ultrafiltration unit, can be operated at normal pressures and flow rates by applying the antimicrobial fluid of this invention to the membrane until the measured flow rate of liquid through the membrane reaches levels indicating that the yeast or other microorganisms have been killed and the resulting plugging has been removed. Once normal operation is achieved the antimicrobial composition can optionally be flushed from the unit and the unit can be returned to service without bacterial contamination.

Alternatively the membranes substantially free of microorganism colonies, in reverse osmosis or ultrafiltration units, can be contacted with the antimicrobial composition during periods when the unit is not in operation to prevent any substantial formation of harmful plugging colonies. Accordingly, at the end of a period during which the unit is used, the unit can preferably be flushed with water and detergents to remove organic and inorganic constituents, and contacted with the antimicrobial compounds of this invention to kill microorganisms which otherwise would grow on or in the membrane during downtime. In order to resume operation of the unit, the unit can preferably be flushed with water to remove the antimicrobial composition and the liquids to be either purified or concentrated, by the membrane, can again be applied without reduced efficiency caused by microorganism plugging.

The inventive aspects of the membrane preservatives of this invention will be further exemplified by reference to the following operating Examples which include a preferred embodiment.

EXAMPLE I

Into a suitable blending unit was placed 100 parts of water, 0.563 parts of sodium metabisulfite ($Na_2S_2O_5$), 0.298 parts of citric acid (2,hydroxy-1,2,3-propane tricarboxylic acid), 0.134 parts of sodium acetate, and 0.005 parts of a surface active agent, comprising the reaction product of nonylphenol and about 12 moles of ethylene oxide (T-DET N-12, a nonionic surfactant product of the Thompson Hayward Chemical Company). The chemicals in the blending unit were mixed until the contents were uniform.

EXAMPLE II

Into a suitable dry blending unit was placed 56.3 parts of sodium metabisulfite ($Na_2S_2O_5$), 29.8 parts of citric acid (2,hydroxy-1,2,3-propane tricarboxylic acid), 13.4 parts of sodium acetate, and 0.5 parts of a surface active agent, comprising the reaction product of nonylphenol and about 12 moles of ethylene oxide (T-DET N-12, a nonionic surfactant product of the Thompson Hayward Chemical Company). The chemicals in the dry blending unit were mixed by operating the dry blending unit until the contents were uniform.

EXAMPLE III

A liquid concentrate is prepared by dissolving about 50 parts by weight of the dry blended composition of Example II in about 50 parts by weight of water.

EXAMPLE IV

A quantity of a liquid antimicrobial composition to be used in preventing microbiological growth on a reverse osmosis membrane is prepared by dissolving 25 lbs. of the dry blend of Example II in 100 gallons of water. The pH of the solution is 3.6.

EXAMPLE V

A quantity of a liquid flush composition that is used in a ultrafiltration membrane unit to kill microbial growth by pumping the composition through the membrane is prepared by dissolving 6 lbs. 4 oz. of the dry blend of Example II in 100 gallons of water. The pH of the solution is 4.0.

EXAMPLE VI

A quantity of a liquid antimicrobial composition that is used in a reverse osmosis unit to kill microbial growth on the membrane is prepared by dissolving 6 lbs. 4 oz. of the dry blend composition of Example II in 100 gallons of water. The pH of the solution is 4.0.

EXAMPLE VII

In a reverse osmosis plant cheddar cheese whey at an average incoming solids content of 6.25% and operating at 100° F. on the whey stream, it was discovered that the solids concentration in the whey stream fell from 11.5% to 9%. Examination of the membrane surface showed that the membrane surface was clean. At this time the presence of growth in the membrane backing was noted. A microscopic examination of the material showed the presence of yeast growing in the backing. The composition of the invention was applied to the membranes by preparing a solution which contained ½ oz./gallon of the composition of Example I. The solution was circulated through the unit under a pressure of 550 psi for 30 minutes. The unit was then shut down and allowed to soak with the composition of the invention remaining in the unit for 20 hours. After three successive applications on weekends, the solids content of the concentrate rose to about 11.5% and the yeast growth was no longer present. A decrease in the operating pressure of 100 psi was noted while the solids content of the concentrate increased from 9 to 11.5%.

Many variations can be made in the specific embodiments of this invention by one skilled in the art without departing from the spirit or scope of the invention. Accordingly, the foregoing description and Examples are exemplary of applicant's invention. However, the invention is embodied in the claims hereinafter appended.

I claim:

1. An antimicrobial composition, which prevents the growth of or destroys microorganisms in and on semipermeable membranes, which comprises an aqueous solution of an effective antimicrobial amount of sulfurous acid or a sulfurous acid-yielding compound and an effective concentration of a buffer sufficient to maintain the pH of the aqueous solution less than about 4.5.

2. The antimicrobial composition of claim 1 wherein the sulfurous acid-yielding compound comprises sodium sulfite, sodium sulfite hydrate, sodium bisulfite, sodium metabisulfite, sulfur dioxide or mixtures thereof.

3. The antimicrobial composition of claim 1 wherein the buffer comprises a water soluble polycarboxylic acid and a water soluble ammonium or alkali metal salt of carboxylic acid.

4. The antimicrobial composition of claim 3 wherein the water soluble polycarboxylic acid comprises citric acid, oxalic acid, maleic acid, ethylenediamine tetraacetic acid or mixtures thereof.

5. The antimicrobial composition of claim 3 wherein the water soluble ammonium or alkali metal salt of the carboxylic acid comprises ammonium or an alkali metal acetate.

6. The antimicrobial composition of claim 1 wherein there is about 0.01 to 10 wt-% of sulfurous acid or sulfurous acid yielding compound in the aqueous solution.

7. The antimicrobial composition of claim 1 wherein the pH of the aqueous solution is maintained at less than 3.5.

8. The antimicrobial composition of claim 1 wherein the pH of the aqueous solution is maintained at about 2.0-3.5.

9. The antimicrobial composition of claim 1 wherein the aqueous solution also contains an effective wetting amount of a surfactant.

10. An antimicrobial composition which prevents or destroys the growth of microorganisms on a semipermeable membrane which comprises:
(a) a major portion of water;
(b) about 0.01 to 50 wt-%, based on the composition, of sulfurous acid or a sulfurous acid yielding compound selected from the group comprising sodium sulfite, sodium bisulfite, sodium metabisulfite, sulfur dioxide and mixtures thereof;
(c) an amount of citric acid and sodium acetate sufficient to maintain the pH of the composition in the range of about 2.0-4.5; and
(d) about 0.0001 to 1.0 wt-%, based on the composition of a surfactant.

11. The composition of claim 10 wherein the surfactant is nonionic, anionic or amphoteric.

12. The composition of claim 10 wherein there is about 0.01 to 5.0 wt-% of citric acid and 0.01 to 5.0 wt-% sodium acetate, based on the composition.

13. A process for operating a unit having a semipermeable membrane subject to the growth of microorganisms, which comprises (a) detecting, on a semipermeable membrane which was in contact with a fluid which supports the growth of microorganisms the presence of a membrane plugging amount of a microorganism and (b) contacting the membrane with the antimicrobial composition of claims 1 or 10.

14. A dry blend antimicrobial composition, which when dissolved in water provides a solution that prevents or destroys microorganism growth in or on semipermeable membranes, which comprises an effective antimicrobial amount of sulfurous acid or a sulfurous acid-yielding compound and a calcium sequestering, antimicrobial buffer system which provides the solution with a pH of less than about 4.5.

15. The composition of claim 14 wherein the sulfurous acid-yielding compound comprises sodium sulfite, sodium sulfite hydrate, sodium bisulfite, sodium metabisulfite, or mixtures thereof.

16. The composition of claim 14 wherein the antimicrobial buffer system comprises a water soluble polycarboxylic acid and an ammonium or alkali metal salt of a water soluble carboxylic acid.

17. The composition of claim 14 wherein the polycarboxylic acid is a dicarboxylic acid comprising citric acid.

18. The composition of claim 14 wherein the ammonium or alkali metal salt of the carboxylic acid comprises ammonium or an alkali metal acetate.

19. An aqueous concentrate of the antimicrobial composition which comprises water and about 50-90 wt-% of the dry blend antimicrobial composition of claim 13.

* * * * *